United States Patent [19]
Hauser

[11] Patent Number: 4,763,650
[45] Date of Patent: Aug. 16, 1988

[54] INSTRUMENT FOR INSERTING A DEFORMABLE LENS INTO THE EYE

[76] Inventor: Stephen G. Hauser, 24009 Ventura Blvd., Suite 200, Calabasas, Calif. 91302

[21] Appl. No.: 5,105
[22] Filed: Jan. 20, 1987
[51] Int. Cl.⁴ .............................................. A61B 17/00
[52] U.S. Cl. ............................... 128/303 R; 128/330; 128/354; 128/321; 604/57; 623/6
[58] Field of Search ................... 128/303 R, 330, 354, 128/321, 356; 604/57, 59, 60, 11–18; 623/6

[56] References Cited

U.S. PATENT DOCUMENTS

| | | | |
|---|---|---|---|
| 1,168,115 | 1/1916 | Rueckert | 128/354 |
| 1,284,060 | 11/1918 | Culman | 128/354 |
| 2,137,710 | 11/1938 | Anderson | 128/354 |
| 3,744,883 | 7/1973 | Williams | 128/354 |
| 3,844,291 | 10/1974 | Moen | 128/354 |
| 4,681,102 | 7/1987 | Bartell | 128/303 R |

Primary Examiner—Dalton L. Truluck
Assistant Examiner—Denise Whelton
Attorney, Agent, or Firm—Keith D. Beecher

[57] ABSTRACT

An instrument for inserting a deformable intraocular lens into the eye, and which is constructed so that the deformable lens is grasped in its undeformed state by two jaws which are forced together by a ramp thereby deforming the lens, as the jaws are drawn into a tube, the deformed lens being held in position by the confinement of the jaws by the tube. The jaws and deformed lens are inserted through an incision into the eye using the walls of the small incision to help compress the jaws and the lens. The jaws and the lens are then left inside the eye with the jaws being detached from the instrument. Part of the jaws protrude from the eye to allow the surgeon to remove the jaws from the eye leaving the lens inside the eye.

4 Claims, 2 Drawing Sheets

INSTRUMENT FOR INSERTING A DEFORMABLE LENS INTO THE EYE

BACKGROUND OF THE INVENTION

A deformable intraocular flexible lens has recently been developed for implantation into the eye. Such a lens is inserted into the eye through a small incision made by the surgeon in the sclera or cornea. a typical insertion method is described, for example, in Staar U.S. Pat. No. 4,573,998.

A problem has arisen in the past in that the lens itself has a diameter of the order of 6 millimeters, and the surgeon would prefer to use a smaller incision, because the smaller the incision the more rapid the healing, resulting in more rapid visual and physical rehabilitation and fewer complications. There is also less astigmatism, less discomfort to the patient, a shorter operating time, and thus a reduced cost, when a small incision is used.

The intraocular flexible lens referred to above may be deformed to a reduced configuration for insertion into the eye through a relatively small incision. The lens is provided with haptics or loops which serve to secure the lens in position after it has been inserted into the eye. These haptics or loops, as well as the optical zone of the lens, are fragile, and they have a tendency to tear when attempts are made to deform the lens for insertion purposes. If a lens is damaged during insertion the incision must be enlarged to allow the first lens to be removed and a second lens inserted. This poses a significant problem in devising a suitable instrument for deforming the lens prior to insertion through the small incision, which has no tendency to damage the lens during the deformation process.

Prior art attempts to provide insertion instruments which do not have a tendency to tear off the haptics or loops, or to otherwise damage the lens, have, for the most part, proven to be somewhat unsuccessful.

One such prior art instrument, for example, requires that the lens be rolled by hand during the surgical procedure and inserted into a tube. A reduction nozzle is then screwed onto the tube, and a viscoelastic material is introduced into the other end of the tube by means of a syringe, thereby forcing the lens into the reduction nozzle. In this manner, the lens is forced into a smaller and smaller cylinder, under pressure created by the syringe forcing the viscoelastic material against the lens, until the lens is finally released at relatively high speed into the eye through a 3 to 3.5 millimeter incision. When this prior art instruemnt is used, the lens frequently tears during the insertion process.

A second prior art instruemnt is similar to the one described in the preceding paragraph, except that a clam-like hinged tube is employed to help form the lens into a tubular or rolled configuration. However, as the hinged tube is closed, there is a tendency to crimp the lens and damage it.

Both prior art instruments described above require hand rolling of the lens. However, any handling of the lens has a tendency to damage it. Moreover, powder from surgical gloves, and other foreign particles, can contaminate the lens. In addition, both prior art instruments described above subject the lens to a substantial pressure as the lens is forced along and squeezed down the tube into the eye.

An objective of the present invention is to provide a simple, inexpensive instrument, which may be disposable, for deforming the lens and thereby reducing its configuration without any need for the surgeon or assistant to handle or touch the lens, and which permits the insertion of the lens into the eye through a small incision, all without any tendency to tear off the haptics or loops, or otherwise to damage or contaminate the lens.

DETAILED DESCRIPTION OF THE ILLUSTRATED EMBODIMENT

In the practice of the invention the lens to be inserted into the eye of a patient is delivered to the surgeon in a sterile package. Also included in the package is a disposable insertion instrument constructed in accordance with the teachings of the present invention, and other elements required for loading the lens into the instrument. The instrument is effective in deforming the lens from a flat configuration into a compressed shape, as the lens is loaded into the instrument, to enable the lens to be inserted by the instrument into the eye through a relatively small incision.

The jaws of the instrument of the invention are required to reduce the size of the lens from 6 millimeters to 4 millimeters, or less, for example, during the loading operation, so that the lens may be inserted into the eye through a small incision. during the insertion operation, the forward ends of the jaws must be inserted through the incision, along with the deformed lens. Thus a criterion for the insertion portion of the instrument is it must be very thin, to enable it and the deformed lens to fit into the small incision. This precluded the use of tweezer-like instruments for the insertion process, because any tweezer jaws made to the required thinness would have no squeezing force.

Accordingly, the instrument of the present invention utilizes a hard wall ramp 2 mounted on the tray, which is used in conjunction with extremely thin detachable lens-holding jaws. As the jaws are drawn along the ramp and into a tube during the loading operation, they are forced by the ramp and tube to close around the lens and deform the lens into the desired compact configuration. The detachable jaws may be injection molded or stamped. They are formed of an appropriate material and of a configuration that they re-open when the retaining force against them has been removed.

Figure 1:
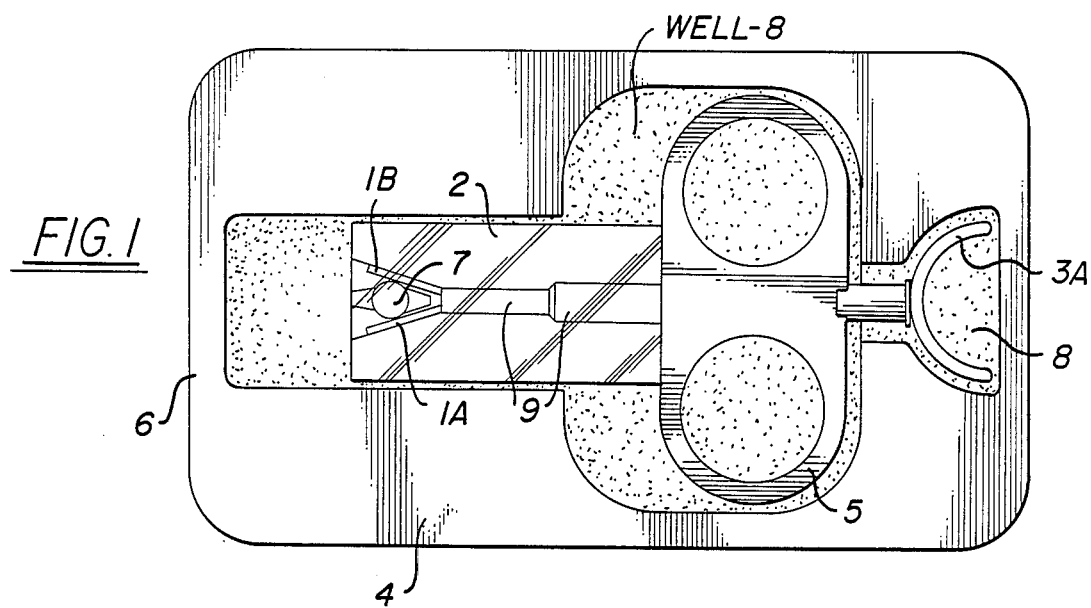
FIG. 1 is a top plan view, partly in section, of the lens insertion instrument of the invention supported on a tray, which also supports other elements, after the instruments has first been removed from a sterile package in which it is received.
Figure 5A:
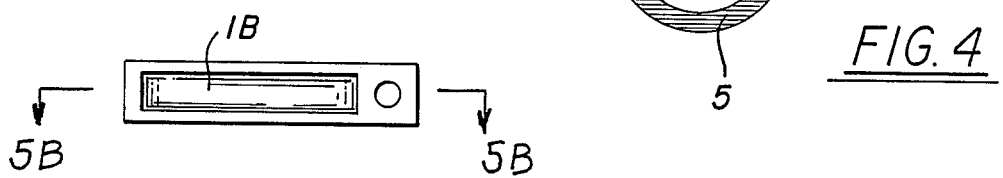
FIG. 5A is a side elevation of one of two like jaw elements of the instrument which is removably mounted on the distal end of a plunger contained in the instrument of FIG. 4.
Figure 5B:
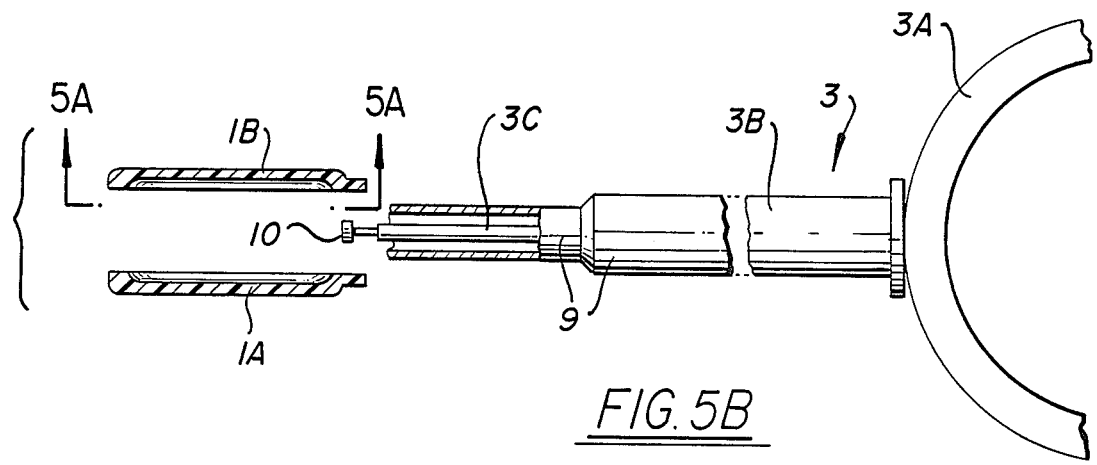
FIG. 5B is an exploded view showing the a section of the jaw element of FIG. 5A, taken along the line 5B—5B of FIG. 5A, and also showing other elements associated with the instrument of FIG. 4.
Figure 2:
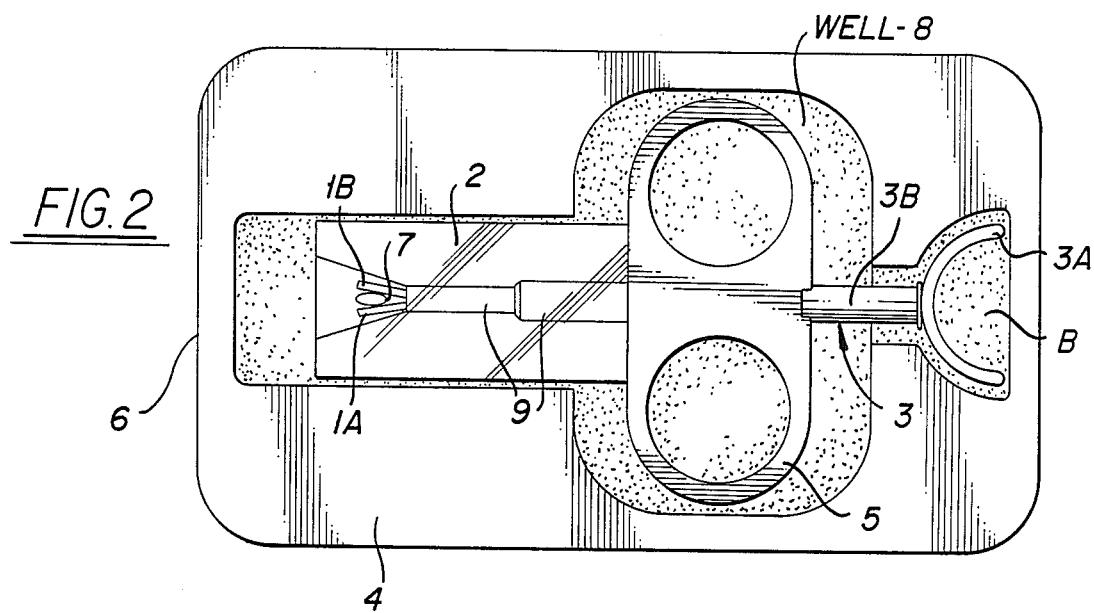
FIG. 2 is a top plan view, partly in section, of the instrument still supported in the tray, and in a partially loaded position.
Figure 3:
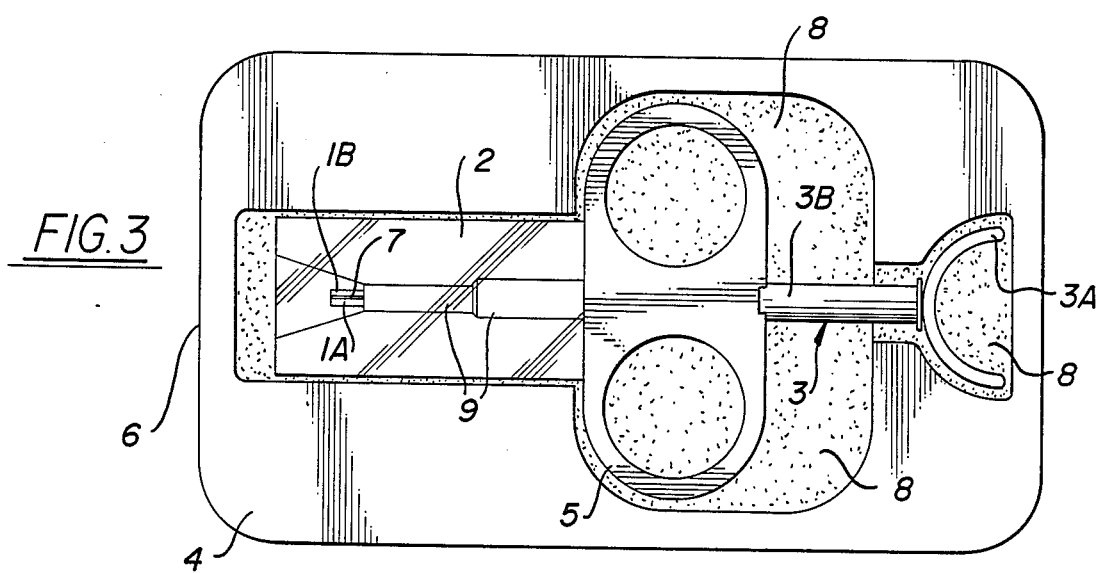
FIG. 3 is a view, like FIGS. 1 and 2, of the instrument still supported in the tray, and in a fully loaded position.

The detachable jaws are designated 1A and 1B in FIGS. 1–3 and in FIGS. 5A and 5B. As best shown in FIG. 5B they are removably attached to a plunger 3 by a post 10. Plunger 3, as shown in FIG. 5B, is made up of a handle portion 3A at one end, and elongated portions 3B and 3C. The jaws 1A and 1B are removably attached to the end of portion 3C. Each jaw has a hole at one end that allows the jaw to pivot around a corresponding right-angle ear on post 10.

Figure 6B:
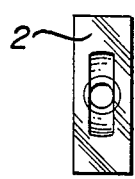
FIG. 6B is a front view of the ramp of FIG. 6A taken along the lines 6B—6B.
Figure 6A:
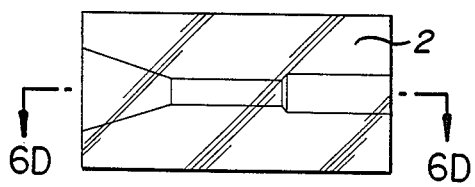
FIG. 6A is a top plan view of a ramp element which is mounted on the tray in FIGS. 1, 2 and 3.
Figure 6C:
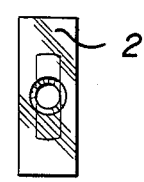
FIG. 6C is a rear view of the ramp taken along the lines 6C—6C of FIG. 6A.
Figure 6D:
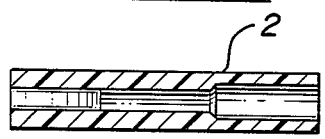
FIG. 6D is a sectional view taken along the line 6D—6D of FIG. 6A.

The plunger and jaws are initially placed in a recess 8 of a sterile tray 4. Ramp 2 is also mounted in recess 8 of the tray. The ramp 2 is a separate element, and is shown in FIGS. 6A, 6B and 6C. It may be formed of acrylic, or other appropriate plastic or other material. When the assembly is first received, a protective covering (not shown) is removed from the tray 4, and the doctor or nurse places his or her index fingers into the holes of a ring guide 5, and his or her thumbs against the forward edge 6 of the tray 4. The ring guide 5 and ramp 2 are then pulled together in a forward direction toward the forward edge 6, and plunger 3 moves to pull the jaws 1A and 1B into a thin walled tube 9 which is attached to the ring guide 5.

This action moves the ramp 2 and thin walled tube 9 toward the forward edge 6 of the tray 4, as shown in FIGS. 2 and 3. The ramp 2 moves, for example, a predetermined distance of, for example, ¾ of an inch, while the detachable jaws 1A and 1B, and plunger 3 remain stationary. The resulting ramping action of ramp 2 guides the detachable jaws 1A, 1B into the end of thin walled tube 9, and tube 9 causes the jaws to compress around a lens 7. This action deforms the lens, and creates a smaller lens configuration as the jaws 1A and 1B are drawn into the end of thin walled tube 9. The lens is now tightly held in its reduced configuration between the detachable jaws 1A, 1B.

As the stroke continues, the detachable jaws 1A, 1B are drawn almost completely into thin walled tube 9, and plunger 3 is displaced outwardly from the ring guide 5, as shown in FIG. 3. The right-hand end of each of the detachable jaws 1A, 1B is angled to allow the jaws to open to their full extent when unrestricted, and yet to remain attached to the ears of post 10 while inside restricting tube 9. Accordingly, as the plunger is pulled back, the jaws 1A, 1B close around the lens.

Figure 4:
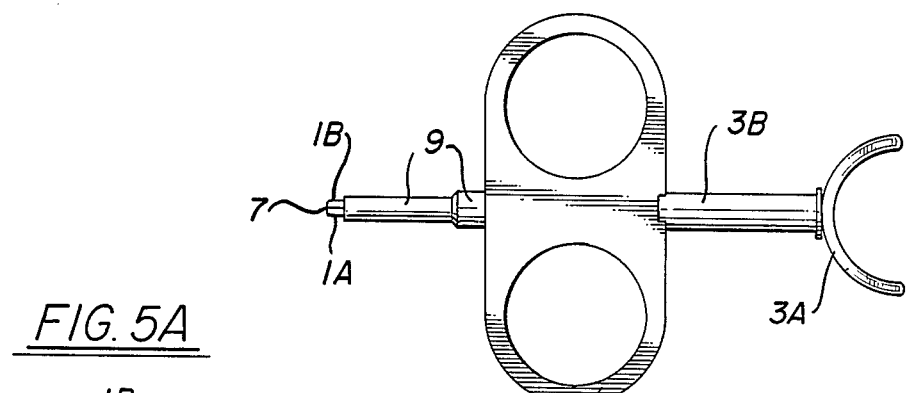
FIG. 4 is a top plan view of the instrument in its fully loaded position, removed from the supporting tray of FIGS. 1, 2 and 3, the instrument now being ready for use by the surgeon to insert the lens into the eye of the patient.

The instrument is now loaded, and it is removed from the tray 4 and from the ramp 2. The loaded intrument, as shown in FIG. 4, is now handed to the surgeon. The detachable jaws 1A and 1B and lens 7 are now contained in the tube 9, and plunger 3 is displaced out from the guide ring 5. The surgeon then holds the guide ring 5, and inserts the ends of the detachable jaws 1A, 1B, containing the deformed lens 7, into the small incision in the eye. The walls of the small incision are used to help compress the detachable jaws and lens as they are advanced from the end of tube 9 into the eye as the surgeon presses handle 3A of plunger 3 in the forward direction. The detachable jaws are advanced out through the end of tube 9 and into the eye, the compressed lens now causes the detachable jaws to spread, after lens 7 is located within the eye. The jaws 1A, 1B, become detached from the plunger when they are pushed out of tube 9 by plunger 3. Accordingly, when tube 9 is moved backwards from the incision, the plunger 3 is detached from the detachable jaws, leaving the lens inside the eye, and also leaving the forward ends of the detachable jaws in the eye. The surgeon subsequently removes the jaws 1A and 1B from the eye through the incision.

The instrument of the invention can be constructed so that it and the lens to be inserted are delivered in a sterile disposable package, with the lens being held in its undeformed state in the detachable jaws 1A, 1B within the ramp 2. Prior to insertion, the jaws are pulled along the ramp 2 which gradually closes the jaws and gradually causes the jaws to be deformed into a reduced configuration. The jaws and the deformed lens are then drawn into the small diameter delivery tube 9. As described above, the instrument is now loaded and ready to insert the front ends of the jaws 1A, 1B into the eye through a small incision. The jaws are then pushed out through the forward end of the tube 9 into the eye, freeing the jaws so that they spread and release the lens, and become detached from the plunger. The lens now re-assumes its original size within the eye, the detached jaws are then withdrawn through the incision, and the lens is manipulated into its proper position by the surgeon. It may be necessary for the surgeon to use a second instrument, inserted into the eye through a second very small incision, to secure the lens in the eye as the detachable jaws are withdrawn.

The invention provides, therefore, an instrument by which an intraocular flexible lens is surrounded by two detachable jaws which are caused to deform the lens by a hard walled ramp, as the jaws are drawn into a tube by a plunger. The lens is now held in its deformed condition by the jaws due to the action of the tube. The jaws, and the end of the tube, are then inserted into the eye using the incision to help compress the lens within the jaws. The lens is then left inside the eye with the jaws protruding partially from the incision and being detached from the instrument. This permits the surgeon at his leisure to remove the jaws from the eye leaving the lens inside.

An important feature of the instrument of the invention is that it permits a one-handed operation to be used to insert the lens into the eye.

In accordance with the invention, the intraocular lens and insertion instrument are delivered to the surgeon in a sterile package so that the lens is never touched by hand, or by an extraneous instrument, thereby insuring that the lens is completely uncontaminated so far as micro-organisms and particulate matter are concerned, all of which results in an extremely safe method and means for the delivery of the lens into the eye.

An important aspect of the instrument of the invention is that it permits the insertion of the lens into the eye without the lens having to move through a confined tube as it moves into the eye.

It will be appreciated that while particular embodiments of the invention have been shown and described, modifications may be made. It is intended in the claims cover all modifications which come within the true spirit and cope of the invention.

I claim:

1. An instrument for inserting a deformable intraocular lens through a small incision into the eye, the incision having a reduced diameter with respect to the diameter of the lens, and the lens being inserted through the incision in a deformed configuration, said instrument including: a tube; a plunger positioned coaxially within said tube for axial movement with respect to said tube; clamping means attached to the distal end of said plunger in axial relationship therewith, said clamping means comprising a pair of normally open jaws which are closed against one another as said clamping means is moved into said tube by said plunger; said clamping means being moved axially in and out of said tube upon reciprocal movement of said plunger and said tube; and an undeformed deformable intraocular lens positioned in said clamping means to be deformed thereby as said clamping means is moved into said tube by said plunger.

2. The instrument defined in claim 1, in which said jaws are detachable from said plunger.

3. The instrument defined in claim 1, and which includes a tray defining a well for supporting the plunger and the clamping means, a ramp member mounted in said well of said tray, said ramp member defining a shaped passage surrounding said plunger and said clamping means for guiding said clamping means into said tube as said clamping means is moved into said tube by said plunger.

4. The instrument defined in claim 2, in which said detachable jaws normally have a spread-apart configuration when positioned out of the confines of said tube, and in which said detachable jaws return to said spread-part configuration when they are moved out of the confines of said tube.

* * * * *